United States Patent [19]

Onouchi et al.

[11] Patent Number: 4,898,781
[45] Date of Patent: Feb. 6, 1990

[54] WATER-SOLUBLE MICROCAPSULES

[75] Inventors: Takashi Onouchi, Tokyo; Hironori Sugai, Yokohama; Kazuo Sekiguchi, Nagareyama; Yoshikazu Hosoda, Fujisawa; Eiichi Yoshida, Tokyo, all of Japan

[73] Assignee: Showa Denko K.K., Tokyo, Japan

[21] Appl. No.: 118,004

[22] Filed: Nov. 9, 1987

[30] Foreign Application Priority Data

Nov. 7, 1986 [JP] Japan .................................. 61-263842

[51] Int. Cl.$^4$ ........................ A61K 37/48; B01J 13/02; C12N 11/08
[52] U.S. Cl. .................... 428/402.22; 252/8.8; 252/174.12; 252/174.13; 252/321; 252/358; 252/550; 252/551; 252/DIG. 13; 252/DIG. 14; 424/94.3; 435/182
[58] Field of Search .............. 428/402.22; 252/174.12, 252/174.13; 424/94.3; 435/182

[56] References Cited

U.S. PATENT DOCUMENTS

| | | | |
|---|---|---|---|
| 3,629,140 | 12/1971 | Bayless et al. | 428/402.22 X |
| 3,819,528 | 6/1974 | Berry | 252/174.12 X |
| 4,107,071 | 8/1978 | Bayless | 428/402.22 |
| 4,244,836 | 1/1981 | Frensch et al. | 428/402.22 X |
| 4,269,729 | 5/1981 | Maruyama et al. | 428/402.22 |

FOREIGN PATENT DOCUMENTS

| | | | |
|---|---|---|---|
| 517123 | 2/1972 | Switzerland . | |
| 1242247 | 8/1971 | United Kingdom | 252/99 |
| 1390503 | 4/1975 | United Kingdom . | |

Primary Examiner—Richard D. Lovering
Attorney, Agent, or Firm—Oblon, Spivak, McCelland, Maier & Neustadt

[57] ABSTRACT

Water-soluble microcapsules using a water-containing hydrophilic substance as a core material and at least one member selected from the group consisting of polyvinyl alcohol and modified polyvinyl alcohols as a coating material are stably retained in a concentrated aqeuous solution and are dissolved in water or a dilute aqueous solution.

3 Claims, No Drawings

WATER-SOLUBLE MICROCAPSULES

BACKGROUND OF THE INVENTION

Field of the Invention

This invention relates to water-soluble microcapsules. More particularly, this invention relates to water-soluble microcapsules which are stably retained in a concentrated aqueous solution containing an agent such as a surfactant and are readily dissolved in water or a dilute aqueous solution.

Numerous proposals have been made to date concerning the microcapsulation of enzymes. One of the methods so far proposed effects the microcapsulation of an enzyme by dispersing the enzyme and swelling particles in a liquid binder and spray drying the resultant dispersion (Japanese Patent Publication SHO 46(1971)-42594). The microcapsules produced by this method provide necessary protection for the enzyme so long as they are in a dry state. In water, they are dissolved to release the enzyme into the water. Another method effects the microcapsulation of an enzyme by dissolving the enzyme and an inorganic salt in a water-soluble liquid binder and spray drying the resultant solution (Japanese Patent Publication SHO 50(1975)-22506). The microcapsules obtained by this method protect the enzyme while in a dry state and dissolve in water to release the enzyme. A granular enzyme preparation proposed for use in a detergent is provided with a coating layer made of modified cellulose which is insoluble in water while in a neutral or acidic state and soluble in water while in an alkaline state (Japanese Patent Publication SHO 61(1986)-44471). All these conventional products are intended to contain an enzyme stably in a dry state therein and to be incorporated in a detergent similarly in a dry state. None of these prior techniques contemplates incorporating an enzyme in systems such as liquid detergent which contain water.

Inventions directed to effecting incorporation of detergent aids other than enzymes as contained in microcapsules have also been disclosed.

For example, a composition taught by one of these inventions is obtained by a process which comprises coating a cationic agent as with dextrin thereby forming microcapsules sensitive to water and incorporating the microcapsules in an anhydrous anionic shampoo (Japanese Patent Public Disclosure SHO 50(1975)-3105). In this case, since the microcapsules by nature release their contents on contact with water, the shampoo intended to incorporate these microcapsules is required to be in an anhydrous state. Microcapsules which are coated with a special copolymer insoluble in an alkaline water and soluble in a neutral or acidic water are also disclosed (Japanese Patent Public Disclosure SHO 61(1986)-28440 and SHO 61(1986)-28441. In the specifications of these inventions, it is stated that when the microcapsules are produced by using a fabric softener or other similar laundry aid as a core material, they can be used for incorporation in detergents. In this case, the microcapsules are intended to permit the fabric softener contained therein to be released therefrom in consequence of changes of the pH value of the laundering liquid at the stages of washing, dehydrating, and rinsing during the course of laundering. Many of the conventional enzyme-containing microcapsules are adapted to encapsulate various enzymes with semipermeable membranes for the purpose of immobilizing the enzymes (Japanese Patent Public Disclosure SHO 52(1977)-3890, SHO 55(1980)-44387, SHO 60(1985)-110330 and SHO 60(1985)-75326). These microcapsules are all insoluble in water.

Many proposals have been made in the field of medical preparations, such as intestinally soluble microcapsules (Japanese Patent Public Disclosure SHO 58(1983)-55413 and SHO 58(1983)-67616) and microcapsules adapted for gradual release of their contents (Japanese Patent Public Disclosure SHO 58(1983)-53110 and SHO 60(1985)-100516).

OBJECT AND SUMMARY OF THE INVENTION

An object of this invention is to provide water-soluble microcapsules which are insoluble in a concentrated aqueous solution such as a liquid detergent and are retained stable therein. Said microcapsules enable a material, which would be degenerated or prevented from producing an expected effect when incorporated directly in concentrated aqueous solution, to be incorporated therein.

To be specific, this invention is directed to water-soluble microcapsules using a water-containing hydrophilic substance as a core material and at least one polyvinyl alcohol selected from the group consisting of polyvinyl alcohol and modified polyvinyl alcohols as a coating material.

The water-soluble microcapsules of this invention which contain an enzyme as the core material, in a concentrated aqueous solution containing a surfactant such as, for example, a liquid detergent or a shampoo, is stably retained therein without being dispersed therein. When they are thrown in water, the polyvinyl alcohol coat thereof is dissolved in the water and the enzyme is dispersed in the water in a state retaining the activity thereof intact.

Now, the water-soluble microcapsules of the present invention will be described in detail below.

Coating Material

The coating material for the microcapsules constitutes one of the most important requirements for the present invention.

To be specific, the polyvinyl alcohol which is used as the coating substance for microcapsules in this invention possesses (i) an average degree of polymerization in the range of 200 to 3,000, preferably 500 to 2,400 and (ii) a saponification ratio of not less than 90%, preferably not less than 95%.

If the degree of polymerization is unduly high, the polyvinyl alcohol exhibits a viscosity so high as to render the handling thereof difficult during the manufacture of microcapsules. If the saponification ratio is unduly low, the microcapsules offer insufficient stability during storage in a water-containing solution. When the microcapsules using a polyvinyl alcohol having a saponification ratio of less than 90% are incorporated in a concentrated aqueous solution, they fail to manifest the required effect because the coat thereof is dissolved or swelled and degenerated.

Any of the modified polyvinyl alcohols can be used as the coating material. Concrete examples of such modified polyvinyl alcohols which are advantageously usable in this invention include cation modified polyvinyl alcohols obtained by the treatment with dimethyl aminopropyl acrylamide and methyl chloride, for example, alkyl modified polyvinyl alcohols obtained by the treatment with vinyl versatate (VEOVA), for example, acid modified polyvinyl alcohols obtained by the treatment with acrylic acid, itaconic acid, for example, and acetacetylated modified polyvinyl alcohols using diketenes, for example.

Treatment With Cross-Linking Agent

Generally, the dissolution rate of a given polyvinyl alcohol in water depends on the degree of polymerization and the saponification ratio of the polyvinyl alcohol. The dissolution rate of microcapsule in water, therefore, can be controlled by suitably selecting a polyvinyl alcohol which possesses a proper degree of polymerization and saponification ratio. The control can also be attained by treating the polyvinyl alcohol with a cross-linking agent.

When desired laundering is effected with a liquid detergent using the microcapsules of this invention which incorporate a fabric softener as a core material, for example, since the fabric softener is a cationic surfactant and affects the anionic surfactant in the detergent, the microcapsules are desired to be dissolved to release the fabric softener into water in the latter stage of the overall process of laundering. In this case, therefore, the dissolution rate of the microcapsules in water can be decreased by treating the polyvinyl alcohol with a cross-linking agent.

Where a modified polyvinyl alcohol is used as the coating material, there are some cases where the modified polyvinyl alcohol may be treated with a cross-linking agent in order for the coat of the produced microcapsules to retain suitable strength.

Examples of the cross-linking agent usable for the treatment include boric acid and boric acid derivatives (such as sodium borate and ethyl borate), aldehyde compounds (such as glyoxal, dialdehyde, and starch), and diepoxides (such as butadiene diepoxide).

Generally, enzymes are not stable against aldehydes and epoxides and, on exposure thereto, may be inactivated. In the encapsulation of an enzyme, therefore, it is desirable to use boric acid or a derivative thereof as the cross-linking agent.

The treatment with a cross-linking agent can be effected by establishing direct contact of microcapsules with a liquid having the cross-linking agent dissolved or dispersed therein or by bringing the cross-linking agent into contact with a solution of polyvinyl alcohol thereby forming the coat of microcapsules.

Though the amount of the cross-linking agent in the coat is not specifically restricted, it is generally adjusted so as to fall in the range of 0.1 to 10% by weight, based on the amount of the polyvinyl alcohol as the coating material.

Hydrophilic Substance (Core Material)

The hydrophilic substance destined to constitute the core material in the water-soluble microcapsules can be any of the compounds which are required only to be compatible with water and are not always required to be soluble in water. Typical examples of the hydrophilic substance usable advantageously include proteins (including enzymes), peptides, amino acids, sugars, gums, surfactants, water-soluble vitamins, water-soluble fungicides, coloring matters, perfumes, defoaming agents, and flocculants. The hydrophilic substance preferably possesses a water content in the range of 5 to 40% by weight based on the core material.

(Enzymes and Supporting Substances)

Now, the encapsulation of enzymes as representatives of the hydrophilic substances enumerated above, will be described below.

Since enzymes are generally in a powdery form, they are not independently encapsulated but are preferably coated in a form dissolved or dispersed in a water-containing polyhydroxy compound.

The selection of a particular enzyme for the encapsulation is carried out in specific consideration of the purpose for which the microcapsules are used. Where the microcapsules are intended for incorporation in a liquid detergent, for example, it is proper to select one enzyme or a mixture of two or more enzymes from the group of enzymes cited below as examples exhibiting activity under neutral or alkaline conditions and contributing to enhancing the deterging power.

Proteases produced by the strains of *Bacillus licheniformis, Bacillus subtilis, Bacillus firmus*, Bacillus sp. FERM. BP-93 (Japanese Patent Public Disclosure SHO 58(1983)-134990), and *Bacillus alcalophlus;*

Amylases produced by the strains of *Bacillus subtilis, Bacillus licheniformis*, and *Aspergillus oryzae;*

Lipases produced by the strains of *Mucor lipolyticus, Candida cylindracea, Pseudomonus nitroreducens, Pseudomonus fragi, Chromobacterium viscosum*, and *Rhizopus delemer* and lipases separated from the spleens of pigs and other similar animals;

Cellulases or hemicellulases produced by the strains of *Bacillus pasteuri, Trichoderma viride*, and *Aspergillus niger*; and Egg white lysozyme and lysozymes produced by the strains such as of *Bacillus subtilis.*

The water-containing polyhydroxy compound to be used in dissolving or dispersing the enzyme acts as a supporting substance for ensuring perfect coating of microcapsules and enhancing the stability of enzyme during storage. The polyhydroxy compound of the foregoing description is a compound having 2 to 6 carbon atoms and containing at least two hydroxyl group or a polymer of the compound. Examples of this compound include polyols and oligomers thereof, sugars, polysaccharide's and glycosides.

As concrete examples of the compound, there can be cited ethylene glycol, propylene glycol, glycerin, butane triol, glucose, fructose, sorbitol, diethylene glycol, triethylene glycol, polyethylene glycol, dipropylene glycol, low molecular weight polyethylene-polypropylene glycol, low molecular weight polyvinyl alcohol, dextrin, pectin, alginic acid, gum arabic, and saponic acid. Among other compounds cited above, ethylene glycol, propylene glycol, glycerin, polyethylene glycol, and low molecular weight polyvinyl alcohol prove to be particularly desirable. One member or a mixture of two or members selected from the group of compounds cited above may be used.

Though the mixing ratio of the enzyme and the polyhydroxy compound is not necessarily defined strictly, the amount of the polyhydroxy compound generally falls in the range of 2 to 50 parts by weight, preferably 5 to 35 parts by weight, based on 1 part by weight of the enzyme.

There are cases where the salt of an alkaline earth metal such as calcium or magnesium proves to be effective in enhancing the stability of the encapsulated enzyme during the storage thereof. Optionally, this salt may be added to the polyhydroxy compound. For example, the salt of a water-soluble or at least partially water-soluble alkaline earth metal such as calcium acetate, calcium chloride, calcium nitrate, magnesium acetate, magnesium chloride, or magnesium nitrate can be used. Though the effect of the alkaline earth metal salt in the stabilization of the enzyme is variable with the kind of the enzyme in actual use, the amount of the alkaline earth metal salt is desired to equal or exceed 5 ppm, based on the amount of the enzyme principle contained in the microcapsules.

In the stabilization of the enzyme, the addition of an antioxidant such as, for example, ascorbic acid or a derivative thereof and a protective colloid-forming substance such as, for example, amino acid, polypeptide or a derivative thereof, or gum is effective. This additive is suitably used when necessary.

Further, the enzyme possesses a stable pH range of its own. For the purpose of retaining the pH value of the contents of the microcapsules within the stable pH range of the enzyme, a salt capable of producing the action of buffer may be added to suit the occasion.

[Surfactant]

As the core material for the microcapsules, a cationic surfactant or an amphoteric surfactant which is used in fabric softener, antistatic agent, surface treating agent, or fungicide can be selected.

As examples of the cationic surfactant, there can be cited trimethyl ammonium lauryl chloride, trimethyl ammonium cetyl chloride, trimethyl ammonium stearyl chloride, dimethyl benzyl ammonium stearyl chloride, and dimethyl ammonium distearyl chloride. As examples of the amphoteric surfactant, there can be cited lauryl betaine and stearyl betaine.

As other examples of the core material for the microcapsules of this invention, there can be cited defoaming agents such as dimethyl polysiloxane, antistatic agents such as aliphatic quaternary ammonium salts, fungicides such as chlorohexydine gluconate, and flocculants such as sodium rosinate and rosin amine acetate.

The aforementioned core material is encapsulated all by itself as a hydrophilic substance or as combined with other hydrophilic substance like polyhydroxy compound serving as a supporting substance.

Method of Encapsulation

The encapsulation can be carried out by any of the conventional methods now in actual use. Now, the main methods available for this purpose will be described below.

(1) A method which forms microcapsules by preparing a water-containing solution of a hydrophilic substance, a supporting substance, and a polyvinyl alcohol substance and bringing this solution into contact with a cross-linking agent or bringing such substances into contact with a dehydrating agent such as alcohol or heating the resultant mixture under a vacuum thereby allowing the polyvinyl alcohol to form a coat. In this case, the polyvinyl alcohol substance is desired to be thoroughly dissolved in the aqueous solution. The water content of this aqueous solution is desired not to exceed 70% by weight, preferably to fall in the range of 60 to 15% by weight. The polyvinyl alcohol content of the aqueous solution is in the range of 3 to 17% by weight, preferably 5 to 12% by weight.

In the encapsulation of an enzyme such as protease, for example, this enzyme and optionally a stabilizer such as a calcium salt are dissolved, in conjunction with the polyvinyl alcohol, in a mixture of a polyhydroxy compound such as propylene glycol with water.

In the encapsulation of a fabric softener, such as a cationic surfactant, specifically dimethyl ammonium distearyl chloride, this cationic surfactant and polyvinyl alcohol are dissolved in water containing ethylene glycol.

The water-containing solution of the aforementioned hydrophilic substance and polyvinyl alcohol can be encapsulated, for example, by any of the following methods.

(i) A method which produces microcapsules by causing the aforementioned solution to fall in the form of minute drops at room temperature into water and/or alcohol (such as ethanol, ethylene glycol, propylene glycol, glycerin, or polypropylene glycol) which has a cross-linking agent such as boric acid dissolved therein advance.

(ii) A method which produces microcapsules by causing the aforementioned solution to be dispersed in the form of minute drops in a hydrophobic solvent (such as benzene, hexane, or liquid paraffin) and heating the resultant dispersion at a temperature approximately in the range of 30° C. to 85° C. under a vacuum to expel water.

(iii) A method which produces microcapsules by dissolving the cross-linking agent in a solvent which fails to mix intimately with water and possesses a hydrophilic group (such as a higher alcohol) and causing the aforementioned solution to be dispersed in the resultant mixed solvent in the form of minute drops.

(iv) A method which produces microcapsules by spraying the aforementioned solution with a spray-drier.

(2) A method which effects production of microcapsules by bringing polyvinyl alcohol or modified polyvinyl alcohol from outside into contact with a water-containing supporting substance having a hydrophilic substance and a cross-linking agent dissolved in advance therein and dehydrating the resultant mixture as with dry air.

To be specific, this method is embodied by causing the water-containing supporting substance having the hydrophilic substance and the cross-linking agent dissolved therein to be spouted out of the central orifice of a two-wall coaxial circular nozzle of a spray-drier and, at the same time, causing an aqueous 15% polyvinyl alcohol or modified polyvinyl alcohol solution to be spouted out of the peripheral orifice of the same circular nozzle.

(3) A method which effects the encapsulation by dissolving or dispersing a hydrophilic substance in a supporting substance which fails to show flowability in a dry state, causing the resultant mixture to form substantially spherical minute drops, and applying an aqueous polyvinyl alcohol or modified polyvinyl alcohol solution on the minute drops.

This method will be described more specifically below. In a supporting substance such as, for example, polyethylene glycol or polyethylene glycol-polypropylene glycol copolymer which exhibits no flowability in a dry state, assumes flowability in a hydrous state, and possesses a melting point in the range of 35° to 80° C., the hydrophilic substance and the cross-linking agent are dissolved or dispersed. Then, the resultant solution or suspension is spray dried at a temperature in the range of 35° to 80° C., preferably 40° to 60° C. to produce substantially spherical minute drops. Subsequently, the minute drops are coated with an aqueous 2 to 10% by weight of polyvinyl alcohol solution by the air-suspension coating method (with a device produced by Coating Place Inc. and marketed under the trademark "Wurster Coating Chamber" or a device produced by Fuji Powder K. K. and marketed under the trademark "New Marumerizer NQ"). The microcapsules consequently obtained are dispersed in propylene glycol containing 10 to 15% of water and then left standing at room temperature for two or three days. At the end of the standing, the water content within the microcapsules nearby equals that of the propylene glycol.

By any of the methods described above, the microcapsules are obtained in a wetted state or fluid state wherein the hydrophilic core substances contains 5 to 40% by weight, preferably 10 to 20% by weight, of water. The average particle diameter of the microcapsules is desired to fall in the range of 20 to 1,000 $\mu m$, preferably 30 to 800 $\mu m$ and most preferably 50 to 500 $\mu m$.

The water-soluble microcapsules of this invention can be usefully applied as an enzyme preparation in dish washer liquid, hard-surface cleaner, shampoo and other water-containing liquid and gel type detergents for household, institutional and industrial use, as an auxiliary agent for fabric softener and the like, and as an enzyme preparation or fungicide in liquid gargle and toothpaste.

The water-soluble microcapsules of the invention can be effectively used in cases where, as discussed above, an auxiliary agent is apt to be deactivated or degraded during long-term contact with the main ingredients of a formulated product. Thus strong demand for the microcapsules can be anticipated.

The microcapsules of the present invention are stably preserved for a long time in a concentrated aqueous solution of a surfactant, a monohydric or polyhydric alcohol, and/or a water-soluble inorganic salt having a water content in the range of 5 to 60% by weight, preferably 20 to 50% by weight. Since the core material and the coating material of these microcapsules are hydrophilic or soluble in water, the microcapsules are quickly dissolved when they are thrown in water (a liquid having a water content of not less than 90%).

The microcapsules of the present invention are not dissolved in a water-containing composition such as, for example, liquid detergent or shampoo and are retained stably for a long time therein. When they are thrown into water, however, they are readily dissolved to release their contents into the surrounding water.

While the conventional enzyme-containing liquid detergents require restriction on the use of anionic surfactants and cationic surfactants because these surfactants inactivate the enzyme, the detergent composition using the microcapsules of this invention permits incorporation therein of any of the surfactants which are usable for ordinary detergents.

Examples of the anionic surfactant include linear sodium alkylbenzene sulfonates (alkyl: $C_{10}$–$C_{16}$) (LAS), sodium $\alpha$-olefin sulfonates (olefin: $C_6$–$C_{22}$) (AOS), sodium alkyl sulfates (alkyl: $C_2$–$C_{17}$) (AS), sodium polyoxyethylene alkyl ether sulfates (alkyl: $C_9$–$C_{17}$; $\overline{EOP}=$1–20) (AES), sodium salt of 2-sulfo-fatty ester (fatty acid: $C_{11}$–$C_{17}$, alcohol: $C_1$–$C_6$) (SFE), sodium secondary alkane-sulfonates (alkane: $C_{12}$–$C_{18}$) (SAS), soaps (fatty acid: $C_{12}$–$C_{18}$), and sodium alkyl phosphates (alkyl: $C_9$–$C_{17}$).

Examples of the nonionic surfactant include polyoxyethylene alkyl ethers (alkyl: $C_5$–$C_{17}$, $\overline{EOP}=$4–20) (AE) and polyoxyethylene alkylphenyl ethers (alkyl: $C_6$–$C_{12}$, $\overline{EOP}$: 4–20) (APE).

Examples of the cationic surfactant include cetyl trimethyl ammonium chloride, stearyl dimethyl benzene ammonium chloride, and distearyl dimethyl ammonium chloride. Examples of the amphoteric surfactant include lauryl betaine and stearyl betaine.

In the production of a liquid detergent containing water-soluble microcapsules of this invention containing an enzyme, this detergent has a basic composition as shown below.

| | |
|---|---|
| Enzyme-containing microcapsules (water-soluble microcapsules of this invention) | 0.01 to 10% (by weight) |
| Surfactant and others | 3 to 70% (by weight) |
| Water | 5 to 60% (by weight) |

The enzyme-containing microcapsules to be incorporated in the detergent are not limited to only one type. It has been heretofore difficult to mix several types of enzymes in a system such as a liquid detergent which contains water. In accordance with this invention, even when protease, amylase, and other enzymes are severally contained in microcapsules and the several types of microcapsules are incorporated altogether in one detergent, they can be retained in a highly stable state during the course of storage of the detergent.

The detergent composition having water-soluble microcapsules of the present invention may incorporate therein, in addition to the aforementioned basic composition and as occasion demands, builders, propylene glycol, ethanol, fluorescent dye, and citric acid which are generally used in detergents as a whole.

Now, the present invention will be described more specifically below with reference to working examples and comparative experiments.

EXAMPLE 1

A solution containing a mixture consisting of the following components was prepared.

| | |
|---|---|
| Protease (API-21) crude powder (activity 105 nkat/mg) | 70 g |
| Calcium acetate | 8 g |
| Propylene glycol | 480 g |
| Polyvinyl alcohol (degree of polymerization 2,000 and saponification ratio 95%) | 55 g |
| Distilled water | 387 g |

This solution was passed through a filter. The resultant filtrate was added dropwise through a small nozzle into a saturated aqueous solution of boric acid, to give rise to microcapsules according with this invention. The microcapsules had diameters approximately in the range of 150 to 800 $\mu m$ and a water content of about 32% by weight. The microcapsules were separated by filtration and stored in propylene glycol containing 25% of water. Then, a liquid detergent composition of the following formula including the propylene glycol having the aforementioned microcapsules dispersed therein was prepared.

| Composition | % by weight |
|---|---|
| Sodium polyoxyethylene alkyl ether sulfate ($C_{14-15}$, $\overline{EOP}=15$) | 15 |
| Polyoxyethylene alkyl ether ($C_{12-15}$, $\overline{EOP}=10$) | 18 |
| Carboxymethyl cellulose | 1 |
| Polyethylene glycol (MW 6,000) | 1 |
| Ethanol | 10 |
| Sodium citrate dihydrate | 8 |
| Dispersion of microcapsules in propylene glycol (average protease activity 4,000 nkat/ml) | 5 |

| Composition | % by weight |
|---|---|
| Distilled water | 42 |

COMPARATIVE EXPERIMENT 1

Protease (API-21) and calcium acetate were dissolved in propylene glycol containing 25% of water to prepare a solution having a protease activity of 4,000 nkat/ml and a calcium ion content of 50 mM. A composition of entirely the same formula as the liquid detergent of Example 1 was produced, except that the solution obtained as described above was used in the place of the dispersion of microcapsules in propylene glycol.

The liquid detergent compositions of Example 1 and Comparative Experiment 1 were left standing at 38° C. (100° F.) for 10 weeks and, at the end of the standing, tested for enzyme activity. The residual ratio of activity was 80 to 85% in the case of the composition of Example 1 incorporating microcapsules and less than 3% (detectable limit) in the case of the composition of Comparative Experiment 1 incorporating propylene glycol solution of protease.

EXAMPLE 2

Solutions A, B and C of the following formulas were prepared by using commercially available lipase separated from porcine spleen (possessing lipase activity of 5,000 U/g, produced by Amano Pharmaceutical Co., Ltd. and marketed under the trademark "Pancreation TA"), amylase (possessing an activity of 220,000 U/g, produced by Yamato Chemical Co., Ltd. and marketed under the trademark "Kleistase M20"), and protease (possessing an activity of 600,000 PU/g, produced by Yamato Chemical Co., Ltd. and marketed under the trademark "Protin AS").

| Composition | A | B | C |
|---|---|---|---|
| Lipase | 5 | — | — |
| Amylase | — | 5 | — |
| Protease | — | — | 8 |
| Calcium acetate | 0.7 | 0.9 | 0.5 |
| Propylene glycol | 45 | 4.5 | 50 |
| Polyvinyl alcohol (degree of polymerization 1,500 and saponification ratio 97%) | 6 | 5 | 6 |
| Distilled water | 43.3 | 44.1 | 35.5 |

Then, the solutions A, B and C were severally added dropwise through a small nozzle into a saturated aqueous solution of boric acid containing 50% of ethanol, to give rise to microcapsules according with the present invention. The microcapsules had diameters in the range of 150 to 500 μm and a water content in the range of 35 to 40%. These microcapsules were given the same treatment as in Example 1 and then preserved in propylene glycol containing 25% of water (dispersions of microcapsules).

Subsequently, liquid detergent compositions of the following formula severally incorporating the aforementioned three types of microcapsules were prepared.

| Composition | % by weight |
|---|---|
| Sodium polyoxyethylene alkyl ether sulfate ($C_{14-15}$, $\overline{EOP}$ = 5) | 10 |
| Polyoxyethylene alkyl ether ($C_{13-15}$, $\overline{EOP}$ = 12) | 25 |
| Sodium salt of coconut fatty acid | 5 |
| Carboxymethyl cellulose | 1 |
| Lipase microcapsules-propylene dispersion (average lipase activity 100 U/ml) | 3 |
| Amylase microcapsules-propylene dispersion (average amylase activity 3,300 U/ml) | 3 |
| Protease microcapsules-propylene dispersion (average protease activity, 1,800 nkat/ml) | 10 |
| Diethylene glycol | 7 |
| Distilled water | 36 |

COMPARATIVE EXPERIMENT 2

A propylene glycol solution having an average lipase activity of 100 U/ml, a propylene glycol solution having an average amylase activity of 3,300 U/ml, and a propylene glycol solution having an average protease activity of 1,800 nkat/ml were prepared by dissolving lipase crude powder, amylase crude powder, and protease crude powder respectively in propylene glycol (containing 25% of water) containing 60 mM of calcium ion. Compositions corresponding to the detergent compositions A, B and C of Example 2 were produced by following the procedure of Example 2, except that the propylene glycol solutions mentioned above were used instead of the dispersion of microcapsules.

The liquid detergent compositions of Example 2 and Comparative Experiment 2 were left standing at 38° C. (100° F.) for 8 weeks and, at the end of the standing, tested for residual ratio of enzyme activity. Consequently, the residual ratios of activity were found to be 75 to 80% for lipase, 80 to 85% for amylase, and 80 to 85% for protease in the case of the compositions of Example 2 incorporating microcapsules and they were invariably less than 3% (detectable limit) in the case of the compositions of Comparative Experiment 2 incorporating the enzymes in the form of propylene glycol solutions.

EXAMPLE 3

A solution containing a mixture consisting of the following components including alkali protease (produced by Sigma Corp. and marketed under product code of "P 5380") was prepared.

| | |
|---|---|
| Alkali protease | 50 g |
| Magnesium chloride | 3 g |
| Calcium chloride | 3 g |
| Sodium ascorbic monophosphate | 4 g |
| Propylene glycol | 450 g |
| Polyvinyl alcohol (degree of polymerization 1,000 and saponification ratio 99%) | 45 g |
| Distilled water | 445 g |

The protease solution thus obtained was added dropwise into a propylene glycol-water mixed solution saturated with boric acid, to give rise to microcapsules (having average particle diameters of 100 to 500 μm and a water content of about 40%) according with the present invention. The microcapsules were separated by filtration and preserved in propylene glycol containing 25% of water.

Then, a gel-like detergent composition of the following formula including the propylene glycol having the microcapsules dispersed therein was prepared.

| Composition | % by weight |
| --- | --- |
| Sodium salt of polyoxyethylene alkyl ether sulfuric acid ($C_{13-15}$ and EOP = 5) | 8 |
| Polyoxyethylene alkyl ether ($C_{13-15}$ and EOP = 10) | 25 |
| Sodium stearate | 3 |
| Sodium citrate dihydrate | 10 |
| Carboxymethyl cellulose | 1 |
| Polyethylene glycol (MW 1,000) | 3 |
| Dispersion of microcapsules in propylene glycol (average protease activity 1,600 nkat/ml) | 10 |
| Propylene glycol | 14 |
| Distilled water | 16 |

COMPARATIVE EXPERIMENT 3

A propylene glycol solution (having a water content of 25%) containing 1,600 nkat/ml of alkali protease (produced by Sigma Corp. and marketed under product code of "P 5380"), 0.3% of calcium chloride, 0.8% of magnesium chloride, and 0.4% of sodium ascorbic monophosphate was prepared. A composition having entirely the same formula as the gel-like detergent of Example 3 was produced by following the procedure of Example 3, except that the propylene glycol solution mentioned above was used instead of the dispersion of microcapsules in propylene glycol.

The gel-like detergent compositions of Example 3 and Comparative Experiment 3 were left standing at 38° C. (100° F.) for 10 weeks and, at the end of the standing, tested for residual ratio of enzyme activity. Consequently, the residual ratio of activity was found to be 90 to 95% in the case of the detergent composition of Example 3 incorporating therein microcapsules and less than 3% (detectable limit) in the case of the detergent composition of Comparative Experiment 3 incorporating the dispersion of protease in propylene glycol.

EXAMPLE 4

Solutions D and E of the following formulas were prepared by using amylase (possessing an activity of 220,000 U/g, produced by Yamato Chemical Co., Ltd. and marketed under the trademark "Kleistase TU 20") and protease (possessing an activity of 500,000 PU/g, produced by Yamato Chemical Co., Ltd. and marketed under the trademark "Thermoase PS").

| Composition | % by weight D | E |
| --- | --- | --- |
| Amylase | 5 | — |
| Protease | — | 5 |
| Calcium acetate | 0.5 | 0.5 |
| Magnesium acetate | 0.5 | 0.5 |
| Diethylene glycol | 45 | 45 |
| Polyvinyl alcohol (degree of polymerization 2,000 and saponification ratio 97%) | 5 | 5 |
| Distilled water | 44 | 44 |

Then, the solutions D and E were severally added dropwise through a small nozzle into a saturated aqueous boric acid solution containing 10% of ethanol and 20% of ethylene glycol, to give rise to microcapsules (having particle diameters in the range of 100 to 400 μm and a water content of about 40%). The microcapsules were separated by filtration and preserved in propylene glycol containing 25% of water.

Subsequently, a tableware grade detergent composition of the following formula including the aforementioned microcapsules was prepared.

| Composition | % by weight |
| --- | --- |
| Sodium dodecyl sulfate | 20 |
| Alcohol ethoxylate ($C_{13-15}$ and EOP = 10 mols) | 20 |
| Carboxymethyl cellulose | 1 |
| Dispersion of microcapsules containing amylase (average amylase activity 3,000 U/ml) | 6 |
| Dispersion of microcapsules containing protease (average protease activity of 1,500 nkat/ml) | 6 |
| Distilled water | 47 |

COMPARATIVE EXPERIMENT 4

A propylene glycol solution having an average amylase activity of 3,000 U/ml and a propylene glycol solution having an average protease activity of 1,500 nkat/ml were prepared by dissolving the same amylase crude powder as used in Example 4 and the same protease crude powder as used in Example 4 in propylene glycol (having a water content of 25%) containing 50 mM of calcium ion. Tableware grade detergent compositions were produced by following the procedure of Example 4, except that the propylene glycol solutions mentioned above were used in the place of the dispersions of the microcapsules containing amylase and protease.

The detergent compositions of Example 4 and Comparative Experiment 5 were left standing at 38° C. (100° F.) for 10 weeks and, at the end of the standing, tested for residual ratio of enzyme activity. Consequently, the residual ratios were found to be 90 to 95% for both amylase and protease in the case of the detergent compositions of Example 4 incorporating therein microcapsules and less than 3% (detectable limit) in the case of the detergent compositions of Comparative Experiment 4 incorporating the enzymes in the form of propylene glycol solutions.

EXAMPLE 5

A solution containing a mixture consisting of the following components including lysozyme separated from egg (produced by Sigma Corp. and marketed under product code "L7001") was prepared.

| | |
| --- | --- |
| Lysozyme | 20 g |
| Calcium chloride | 3 g |
| Propylene glycol | 520 g |
| Sodium ascorbic monophosphate ester | 2 g |
| Polyvinyl alcohol (degree of polymerization 700 and saponification ratio 87%) | 45 g |
| Ethanol | 20 g |
| Distilled water | 390 g |

From this solution, microcapsules according with this invention were produced by the use of a spray-drier provided with a rotary disc type dispersing device. The microcapsules had diameters of about 20 to 100 μm and a water content of about 6%. Then, a shampoo composition of the following formula including the propylene glycol having the microcapsules dispersed therein was prepared.

| Composition | % by weight |
| --- | --- |
| Sodium polyoxyethylene lauryl ether sulfate | 10 |

| Composition | % by weight |
|---|---|
| Sodium stearate | 5 |
| Sodium laurate | 8 |
| Propylene glycol | 47 |
| Ethyl alcohol | 15 |
| Dispersion in propylene glycol of microcapsules containing lisozyme (average lisozyme activity of 400 U/ml) | 5 |
| Distilled water | 10 |

COMPARATIVE EXPERIMENT 5

A propylene glycol solution having a lisozyme activity of 400 U/ml and containing lisozyme, calcium chloride (0.3%) and sodium ascorbic monophosphate ester (0.2%) was prepared. A shampoo composition of entirely the same formula as in Example 5 was produced by following the procedure of Example 5, except that the solution mentioned above was used in the place of the dispersion of the microcapsules containing lisozyme.

The shampoo compositions of Example 5 and Comparative Experiment 5 were left standing at 30° C. for 3 months and, at the end of the standing, tested for residual ratio of enzyme activity. Consequently, the residual ratio was found to be 90 to 95% in the case of the shampoo composition of Example 5 incorporating microcapsules and less than 3% (detectable limit) in the case of the shampoo composition of comparative Experiment 5 incorporating the enzyme in the form of propylene glycol solution.

EXAMPLE 6

A mixed solution of the following formula including a fabric softener was prepared.

| Composition | % by weight |
|---|---|
| Distearyl dimethyl ammonium chloride | 25 |
| Propylene glycol | 14 |
| Polyvinyl alcohol (degree of polymerization 2,000 and saponification ratio 99%) | 5 |
| Distilled water | 56 |

The mixed solution was added dropwise through a small nozzle into a water-alcohol mixture saturated with boric acid, to give rise to microcapsules according with the present invention. The microcapsules were retained in the aforementioned boric acid solution at 35° C. for 20 minutes and then separated therefrom by filtration. The microcapsules were then preserved in propylene glycol containing 20% of water.

The microcapsules were not dissolved in a commercially available liquid detergent (having a water content of 60%) but were dissolved after 15 minutes' immersion in water at 30° C.

EXAMPLE 7

A solution of the following formula including a cationic surfactant possessing an antistatic and sterilizing effect was prepared.

| Composition | % by weight |
|---|---|
| Stearyl trimethyl ammonium chloride | 18 |
| Stearyl dimethylbenzyl ammonium chloride | 10 |
| Ethylene glycol | 15 |
| Polyvinyl alcohol (degree of polymerization 2,400 and saponification ratio 95%) | |
| Distilled water | 52 |

The solution was added dropwise through a small nozzle into water saturated with boric acid and kept at 40° C., to give rise to microcapsules according with the present invention. The microcapsules were left standing continuously in the aqueous boric acid solution for 7 minutes and separated therefrom by filtration and preserved in polyethylene glycol containing 25% of water.

The microcapsules were not dissolved in a commercially available shampoo (having a water content of 40%) but were dissolved after 2 to 4 minutes' immersion in warm water at about 35° C.

EXAMPLE 8

A solution A of the following formula was prepared by using amylase (possessing an activity of 220,000 U/g, produced by Yamato Chemical Co., Ltd. and marketed under the trademark "Kleistate TU 20").

| Composition of Solution A | % by weight |
|---|---|
| Amylase | 5.5 |
| Calcium acetate | 1.5 |
| Sodium borate | 3.0 |
| Polypropylene glycol (average molecular weight 1,000) | 16.0 |
| Propylene glycol | 49.5 |
| Polyethylene glycol (average molecular weight 600) | 12.0 |
| Distilled water | 12.5 |

Separately, a solution B of the following formula including polyvinyl alcohol was prepared.

| Composition of Solution B | % by weight |
|---|---|
| Polyvinyl alcohol (degree of polymerization 600 and saponification ratio 97%) | 5 |
| Polyvinyl alcohol (degree of polymerization 1,500 and saponification ratio 97%) | 6 |
| Distilled water | 89 |

By the use of a spray-drier provided with a two-wall coaxial nozzle, the solution A was spouted through the central orifice of the nozzle and the solution B through the peripheral orifice of the nozzle at the same time, to give rise to microcapsules according with the present invention. The microcapsules had diameters in the range of 80 to 200 μm. The microcapsules were then dispersed in a propylene glycol containing 15% of water and left standing therein for 24 hours and, at the end of the standing, separated therefrom by filtration. They were found to have a water content of about 11%.

EXAMPLE 9

A mixed solution of the following formula was prepared by using protease (possessing an activity of 500,000 PU/g, produced by Yamato Chemical Co., Ltd. and marketed under the trademark "Thermoase PS").

| Composition | % by weight |
|---|---|
| Protease | 7.2 |
| Calcium acetate | 1.8 |
| Magnesium acetate | 0.6 |
| Borax | 18.1 |

| Composition | % by weight |
|---|---|
| Polyethylene glycol (average molecular weight 5,000) | 72.3 |

The polyethylene glycol was a product in the form of flakes and the other components were in the form of microfine particles not more than 10 μm in size. The mixture was dissolved by heating at about 65° C. and converted into minute beads 50 to 120 μm in size by the use of a spray cooling device (produced by Ogawara Manufactory).

The minute beads were coated with an aqueous 3% polyvinyl alcohol (degree of polymerization of 1,500 and saponification ratio not less than 97%) solution with a flow dry coating device (produced by Fuji Powder Co., Ltd. and marketed under the trademark "New Marumerizer NQ"), for encapsulation. The inlet temperature of dry air was 35° C. and the flow rate of the dry air was adjusted to the highest level at which the dry air in motion would not scatter the minute beads. The increase of weight by the encapsulation was about 15%. The microcapsules thus produced were left standing in propylene glycol containing 10% of water at room temperature for 2 days and, at the end of the standing, separated therefrom by filtration. They were found to have a water content of about 8%.

COMPARATIVE EXPERIMENT 9

Microcapsules were produced by following the procedure of Example 6, except that polyvinyl alcohol possessing a degree of polymerization of 1,500 and a saponification ratio of 85% was used instead. In propylene glycol containing 10% of water or in a liquid detergent (having a water content of about 40%), these microcapsules were dissolved after 2 days' standing. In contrast, the microcapsules produced in Example 6 showed no sign of dissolution even after one month's standing under the same conditions.

What is claimed is:

1. Water-soluble microcapsules comprising:
    a core material of hydrophilic substance which comprises an enzyme and a water-containing polyhydroxy compound in an amount of 2 to 50 times that of said enzyme by weight and having a water content of 5 to 40% by weight, said enzyme being dissolved or dispersed in said water-containing polyhydroxy compound; and
    a coating material of polyvinyl alcohol having an average degree of polymerization in the range of 200 to 3,000 and a saponification ratio of not less than 90%.

2. The water-soluble microcapsules according to claim 1, wherein said polyvinyl alcohol has been treated with a cross-linking agent.

3. The water-soluble microcapsules according to claim 1, wherein said polyhydroxy compound is at least one member selected from the group consisting of compounds possessing 2 to 6 carbon atoms and containing two or more hydroxyl groups and polymers of said compounds.

* * * * *